United States Patent
Grasmüller

(10) Patent No.: US 6,211,959 B1
(45) Date of Patent: Apr. 3, 2001

(54) METHOD OF CHECKING FOR THE PRESENCE OF CONNECTION BALLS

(75) Inventor: Hans-Horst Grasmüller, Mammendorf (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/380,444
(22) PCT Filed: Feb. 25, 1998
(86) PCT No.: PCT/DE98/00560
§ 371 Date: Sep. 2, 1999
§ 102(e) Date: Sep. 2, 1999
(87) PCT Pub. No.: WO98/39795
PCT Pub. Date: Sep. 11, 1998

(30) Foreign Application Priority Data

Mar. 5, 1997 (DE) .............................. 197 09 003

(51) Int. Cl.[7] .............................. G01B 11/00; G01N 21/00
(52) U.S. Cl. .......................... 356/390; 356/394; 356/237.4
(58) Field of Search ..................... 356/390, 388, 356/394, 237.1–237.5

(56) References Cited

U.S. PATENT DOCUMENTS

| 4,728,195 | * | 3/1988 | Silver . | |
|---|---|---|---|---|
| 5,450,206 | * | 9/1995 | Caillat et al. . | |
| 5,859,924 | * | 1/1999 | Liu et al. | 382/145 |
| 6,028,671 | * | 2/2000 | Svbetkoff et al. | 356/368 |

FOREIGN PATENT DOCUMENTS

| 0 638 801 | * | 2/1995 | (EP) . |
| 2-81449 | * | 3/1990 | (JP) . |
| 10-89927 | * | 4/1998 | (JP) . |
| WO 96/21343 | * | 7/1996 | (WO) . |

OTHER PUBLICATIONS

Ross et al, "Inspection Technique for Solder Reflow Pad Height/Volume", *IBM Technical disclosure Bulletin*, vol. 22, No. 9, Feb. 1980, p. 4068.*

* cited by examiner

*Primary Examiner*—Frank G. Font
*Assistant Examiner*—Layla Lauchman
(74) *Attorney, Agent, or Firm*—Hill & Simpson

(57) ABSTRACT

Method of checking for the presence of connection balls of components, in particular of ball grid arrays by projecting light obliquely onto the components to create reflections and shadows at the connection balls and any impurities, detecting the reflections and shadows and evaluating the detected shadows and reflections to determine which are from connection balls and which are from impurities.

1 Claim, 1 Drawing Sheet

METHOD OF CHECKING FOR THE PRESENCE OF CONNECTION BALLS

BACKGROUND OF THE INVENTION

The invention relates to a method of checking for the presence of connection balls of components by illuminating the component with the connection balls and detecting reflections and shadows being produced.

In the course of automatically populating substrates, in particular printed circuit boards or ceramic substrates, with SMD components for surface mounting (SMD=Surface Mounted Devices), the components, before being emplaced, are visually inspected with regard to their position and the presence of all the connections, in particular all the connection balls in the case of ball grid arrays (BGAs), in order subsequently to correct the position of the component prior to emplacement on the substrate, or to sort out the component owing to missing connections.

WO 96/21343 discloses an apparatus for identifying the position of the connections of components which uses illumination with light which is obliquely incident on all sides, in order to automatically evaluate the reflections from connection balls and to determine the position of the component so that positional correction can subsequently be performed. In this case, use is made of segmented ring light illumination in order to illuminate all the connection balls uniformly from different sides.

However, this method does not make it possible to determine unambiguously whether all the connection balls are present at the intended contact points. Soldering residues from the fixing of the balls can also cause a reflection which resembles a reflection from a connection ball and simulates a ball that is present. The great dependence of the reflection position on the surface condition of the connection balls additionally makes the evaluation more difficult.

T. Ross et al: Inspection technique for solder reflow pad height/volume, IBM Technical Disclosure Bulletin, volume 22, No. 9, February 1980, page 4068, discloses a method of determining the height or the volume of connection balls on components, where an image-evaluating unit determines the shadow area cast by the connection balls and resulting from obliquely incident illumination. In this case, the illumination is effected only on one side, since if the illumination were on all sides, shadow areas cast by the connection balls and capable of evaluation would not be produced. Dark impurities on the components of the same size as shadow areas lead to misinterpretations concerning the presence of connection balls in the case of this method.

SUMMARY OF THE INVENTION

The object of the invention consists in developing a method of checking, without errors, for the presence of connection balls on components, in particular ball grid arrays (BGAs), with account especially being taken of the erroneous reflections from impurities (soldering residues) on the locations nominally occupied by connection balls.

The object is achieved according to the invention by means of a method having the steps of illuminating the connection balls with an obliquely incident light from one direction, detecting both light reflections and shadows cast laterally and evaluating both the reflections and the shadows to determine the presence of a connection ball.

With the connection balls being illuminated on one side by parallel light or light emitted from a point light source, the resulting shadows and the light reflections from the connection balls are evaluated. To that end, the shadow sizes which are dependent on the illumination direction and the size of the connection balls are to be determined theoretically or experimentally and compared with the instantaneously measured shadow sizes in each case. As a result of this, the influence of the surface condition of the connection balls on the evaluation is additionally avoided, in an advantageous manner. As a result of the illumination on one side, a shadow that can be evaluated for the purpose of checking for the presence of the connection balls is advantageously produced, by comparison with the method for measuring the light reflections which is disclosed in the prior art.

A further advantage of the method consists in the possibility of retrofitting existing evaluation devices for the detection of the light reflection, the illumination device and the image-evaluating unit being adopted. The image analysis is then adapted correspondingly to the novel method.

By detecting the shadow and reflection, not only soldering residues which cause misinterpretable reflections but also dark impurities of the same size as the shadow of connection balls are not identified incorrectly as connection balls that are present. This ensures error-free checking for the presence of the connection balls, independently of the surface condition of said balls.

A configuration according to the invention is elucidated in more detail in the drawings.

DESCRIPTION OF THE PREFERRED EMBODIMENT

Figure 1:
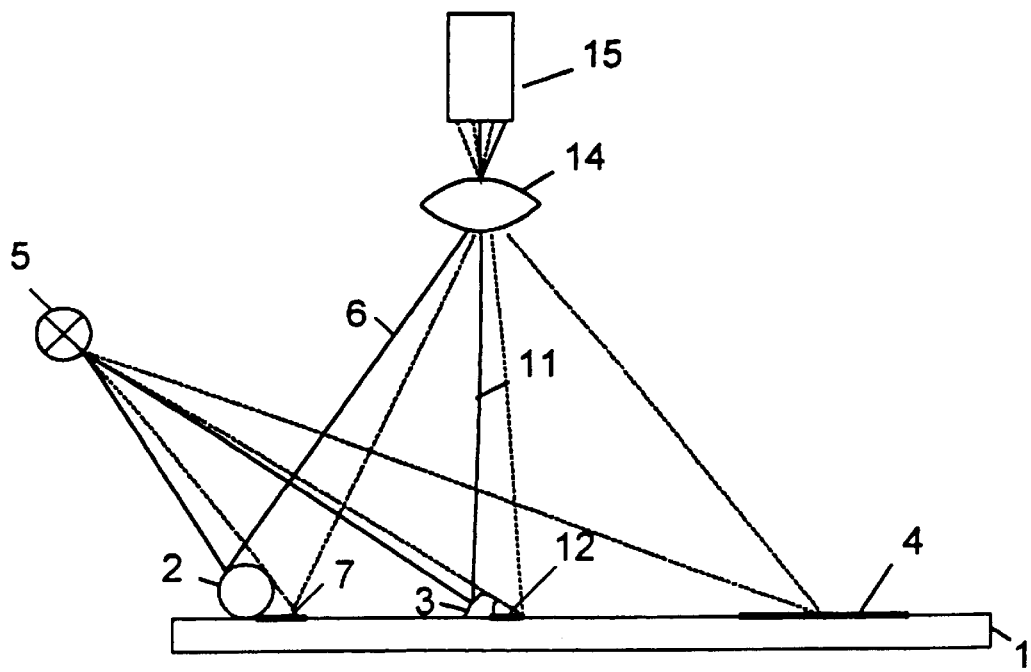
FIG. 1 shows an apparatus for checking for the presence of connection balls, in longitudinal section.

FIG. 1 diagrammatically shows, in longitudinal section, how a component, here a ball grid array 1, with a connection ball 2, a metallic impurity 3 and also a dark impurity 4 of the same size as the shadow of a connection ball is illuminated laterally by a light source 5. Lateral illumination with parallel light can also be used in the method. It is particularly advantageous to use segmented ring light illumination whose segments can be controlled individually in terms of their intensity, thereby obtaining illumination by light which is obliquely incident on one side.

The connection ball 2 produces a reflection 6 and a shadow 7, and the metallic impurity 3 produces a further reflection 11 and a further shadow 12, which—in the same way as a dark impurity 4 of the same size as the shadow of a connection ball—are imaged via an objective 14 onto an image-evaluating unit 15, for example a CCD camera. The size of the further shadow 12 of the metallic impurity 3 differs from that of the shadow of a connection ball that was intended at the location of the metallic impurity, which, with the aid of the image-evaluating unit 15, allows the missing contact to be identified and the component to be sorted out. The dark impurity 4 of the same size as the shadow of a connection ball can be identified by the absence of an additional reflection associated with the dark impurity 4, with the aid of the image-evaluating unit 15.

Figure 2:
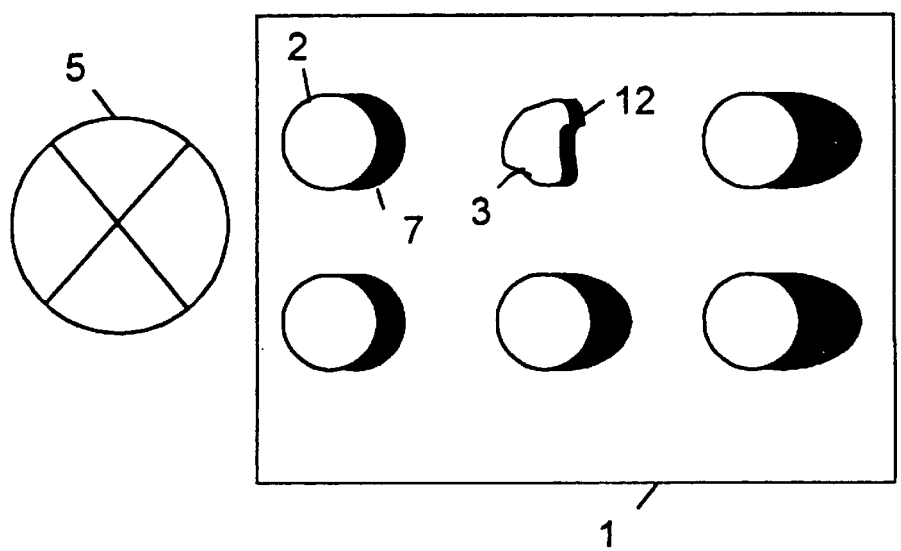
FIG. 2 shows a plan view of a laterally illuminated component with the shadows cast by the connection balls.

FIG. 2 illustrates the laterally illuminated component 1 with a plurality of connection balls 2 with the associated shadows 7 and also the metallic impurity 3 with the associated further shadows 12 from the direction of the image-evaluating unit 15. The further shadow 12 of the metallic impurity 4 differs from an expected shadow cast by a connection ball, which is identified by the image-evaluating unit 15.

What is claimed is:

1. A method of checking for the presence of connection balls on components, including ball grid arrays by illuminating the connection balls by light which is obliquely incident from one direction, detecting light reflections from the connection balls by an image-evaluating unit connected downstream of an imaging optical arrangement and evaluating a shadow cast laterally with respect to the connection balls and resulting due to the obliquely incident light by the image-evaluating unit the improvement comprising using the size of the shadow to be expected given a specific size of the connection ball, in conjunction with the presence of the associated light reflection from the connection ball as a criterion for automatically checking for the presence of connection balls.

* * * * *